(12) United States Patent
Derrieu et al.

(10) Patent No.: US 9,339,460 B2
(45) Date of Patent: May 17, 2016

(54) SELF-EMULSIFIABLE LIQUID FLORFENICOL COMPOSITION INTENDED TO BE INCORPORATED INTO THE DRINKING WATER OF LIVESTOCK

(75) Inventors: Guy Derrieu, Cagnes sur Mer (FR); Bernard Raynier, Nice (FR)

(73) Assignee: VIRBAC SA, Carros (FR)

( * ) Notice: Subject to any disclaimer, the term of this patent is extended or adjusted under 35 U.S.C. 154(b) by 766 days.

(21) Appl. No.: 12/810,758

(22) PCT Filed: Dec. 17, 2008

(86) PCT No.: PCT/FR2008/001757
§ 371 (c)(1),
(2), (4) Date: Sep. 21, 2010

(87) PCT Pub. No.: WO2009/106714
PCT Pub. Date: Sep. 3, 2009

(65) Prior Publication Data
US 2011/0028560 A1    Feb. 3, 2011

(30) Foreign Application Priority Data
Dec. 26, 2007 (FR) ..................... 07 09106

(51) Int. Cl.
| A61K 31/33 | (2006.01) |
| A61K 9/107 | (2006.01) |
| A23K 1/16 | (2006.01) |
| A23K 1/18 | (2006.01) |
| A61K 9/00 | (2006.01) |
| A61K 31/165 | (2006.01) |
| A61K 47/10 | (2006.01) |
| A61K 47/14 | (2006.01) |
| A61K 47/26 | (2006.01) |

(52) U.S. Cl.
CPC ............... *A61K 9/1075* (2013.01); *A23K 1/164* (2013.01); *A23K 1/1813* (2013.01); *A61K 9/0053* (2013.01); *A61K 31/165* (2013.01); *A61K 47/10* (2013.01); *A61K 47/14* (2013.01); *A61K 47/26* (2013.01)

(58) Field of Classification Search
None
See application file for complete search history.

(56) References Cited

U.S. PATENT DOCUMENTS
2004/0052824 A1    3/2004   Abou Chacra-Vernet et al.

FOREIGN PATENT DOCUMENTS
| WO | 9956727 | 11/1999 |
| WO | 02/053131 | 7/2002 |
| WO | 02053131 | 7/2002 |
| WO | 2004014341 | 2/2004 |
| WO | WO 2004/014341 | * 2/2004 | ............ A61K 9/107 |

OTHER PUBLICATIONS

Gosh et al (AAPS PharmSciTech 7:E1-E6, 2006).*
Anon: "glycosyl" [on line] 2 Nov. 2, 2007. Extrait de l'internet: URL: http://en.wikipedia.org/wiki/Glycosyl> [extrait le Sep. 26, 2008] XP002497563.

* cited by examiner

*Primary Examiner* — Craig Ricci
(74) *Attorney, Agent, or Firm* — Volpe and Koenig, P.C.

(57) ABSTRACT

The invention relates to a self-emulsifiable liquid composition intended to be diluted in an aqueous intermediate solution and then incorporated into the drinking water of livestock animals, and also to the use of such a composition. The invention is characterized in that the composition comprises at least—between 1% and 12% by weight of the florfenicol active ingredient, relative to the total volume of the composition; —at least 50% by weight, relative to the total volume of the composition (p/v), of a mixture of C8-C10 saturated polyglycosylated glycerides having an HLB (hydrophilic-lipophilic balance) of less than 16; and—at least 5% by weight, relative to the total volume of the composition (p/v), of a surfactant.

2 Claims, 3 Drawing Sheets

Figure 1:
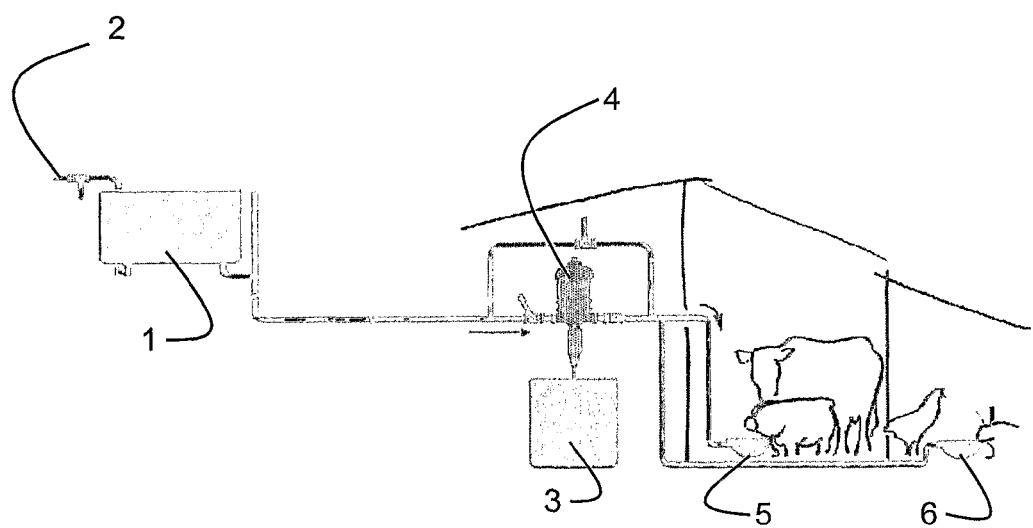

SELF-EMULSIFIABLE LIQUID FLORFENICOL COMPOSITION INTENDED TO BE INCORPORATED INTO THE DRINKING WATER OF LIVESTOCK

This invention relates to a self-emulsifiable liquid Florfenicol composition including the active principle Florfenicol, intended to be incorporated in the drinking water of livestock and, in particular, the drinking water of pigs, poultry, sheep, goats and cattle. It relates more specifically to such a self-emulsifiable liquid Florfenicol composition for veterinary use.

Livestock are subject to all types of diseases, most of which are contagious. Therefore, there is a significant risk, when symptoms appear in one animal, that they will quickly spread to the entire group with which the animal lives, and to groups in the vicinity. In addition, it often appears to be necessary, when a pathology appears in an animal, to quickly treat, at the same time, all of the animals at the same livestock production site, by administering the same curative or preventive treatment.

The route of administration most appropriate for treating a large number of animals, aside from incorporating a drug in dry or moist food, is to incorporate such a drug in the drinking water. Indeed, sick animals continue to drink in order to compensate for hyperthermia and dehydration, even if they have a reduced appetite. Moreover, with respect to dry or moist food, the use of drinking water enables flexibility and continuity of implementation, with dose modulation and treatment combinations. The use of drinking water also ensures better homogeneity of the treatment and better regularity of the dosage. Finally, drinking water also guarantees, with respect to dry or moist food, quick intervention and assimilation of treatments.

The existing intensive livestock productions are, for the most part, equipped with drinking water circulation circuits. These circuits supply toughs suitable for animals of relatively large sizes, such as pigs or calves, or small pipettes more specifically suitable for small animals such as poultry.

To administer Florfenicol in drinking water, in a first step, the set point concentration or usage dose of the Florfenicol in the drinking water is determined by taking into account the prescribed dosage, growth tables as well as the average water consumption of the animals to be treated. Then, the set point concentration having thus been determined, the amount of liquid composition with concentrated active principle is added to the circulation circuit, enabling this set point concentration to be obtained in the troughs or in the pipettes where the animals to be treated come to drink. In general, the administration of the active principle involves a step of preparing an intermediate aqueous dilution in a tank for intermediate dilution of the treatments of the circulation circuit. This intermediate dilution has an active principle concentration of below the active principle concentration of the concentrated liquid composition and above the set point concentration.

The use of a liquid composition with concentrated active principle has numerous advantages. It is perfectly adaptable to the needs of the animals. However, its development requires numerous problems to be solved and is therefore particularly difficult.

In particular, Florfenicol used regularly in the treatment of livestock has low solubility, on the order of around 1.32 g/l, in water at room temperature. This therefore presents a problem for the development of the concentrated liquid composition, but also at the time of the intermediate dilution. Thus, in the intermediate dilution, the Florfenicol concentration is generally much higher than its solubility threshold. This causes in particular heterogeneity in this intermediate dilution, due to sedimentation of the active principle, causing poor distribution of the Florfenicol in the troughs and in the pipettes, but also clogging of the various elements of the circulation circuit, which can occur at the supply tube of a dosing pump, at the control elements enabling automatic activation of the water circulation circuit, and at the pipettes, when the treatment is intended for small animals such as poultry.

It is therefore particularly important for the liquid concentrated Florfenicol composition to be perfectly homogeneous and stable, at all of the dilution stages, and to enable complete dissolution of this active principle to be obtained during the final dilution in the drinking water located in the troughs and pipettes where the animals to be treated come to drink.

For Florfenicol, a structural analog of thiamphenicol, which is a wide-spectrum synthetic antibiotic, primarily bacteriostatic, there are already concentrated compositions such as the NUFLOR® product sold by the Schering-Plough company. These compositions, which contain a Florfenicol concentration of 2.3% by weight with respect to the total volume of the composition (w/v), nevertheless have some of the disadvantages mentioned above.

Thus, the existing compositions do not provide satisfactory solubility of the active principle particles in the troughs and the pipettes of the animals during dilution of the preparation in the drinking water, resulting in more or less crystallization, according to the desired dilution. In addition, such compositions must absolutely be preserved at a temperature below 25° C., and have very limited preservation after dilution in the drinking water.

To solve this problem, one of the solutions provided, disclosed in the international application WO 02/49609, consists of obtaining an aqueous suspension of active principle of which the average particle size is less than 20 microns. This requires a micronized active principle to first be obtained before incorporating it into the suspension. This solution, in consideration of the nature of the active principles, which have a very low dissolution rate, is not entirely satisfactory in the dilution process. Indeed, a sedimentation phenomenon appears in the dilution tank as well as in the troughs and pipettes, which creates a concentration gradient in the drinking water. In addition, it is known to a person skilled in the art that it is very difficult to obtain, except by complex and costly techniques, particles with an average size below 5 microns. This disadvantage makes the application of this solution more complex.

A solution to this stated problem consists of developing a self-emulsifiable liquid composition including an active principle and capable of being subjected to aqueous dilution having an active principle content that may be greater than the solubility limit of the active principle in water, while respecting:

the integrity of the active principle and the homogeneity of the distribution of the active principle in the corresponding dilute;

the physical stability of the corresponding dilute by inhibiting or limiting any sedimentation;

the capacity to transfer the corresponding dilute into the drinking water of the livestock by using available conventional processes;

and by ensuring rapid and complete solubility of the active principle in the drinking water.

This invention is consequently intended to provide a composition containing at least one active principle, Florfenicol, capable of treating intensive livestock, in particular pigs, poultry, sheep, goats and cattle, in the form of a stable, self-emulsifiable liquid composition capable of being introduced into the drinking water circulation circuits of animals, which many livestock production sites have. This self-emulsifiable liquid composition will then evolve during the intermediate dilution into an emulsion that is homogeneous and stable for at least 24 hours, and enable total solubility of the Florfenicol in the drinking water located in the troughs and in the pipettes, where the animals to be treated come to drink, to be obtained quickly. The applicant has observed that, during the intermediate aqueous dilution, the composition of the invention forms an emulsion. The term emulsion as used according to the invention refers to a liquid formed by complete and uniform dispersion of very small particles that give it the properties of the stable colloidal state. The stable colloidal state refers to a substance comprised of very small particles that are dispersed homogeneously in a liquid material, particles resistant to flocculation and aggregation over time.

Thus, the solution proposed according to the invention relates to a self-emulsifiable liquid composition intended to be incorporated in the drinking water of livestock, including at least:
  between 1 and 12% of the active principle Florfenicol by weight with respect to the total volume of the composition (w/v);
  a mixture of C8-C10 saturated polyglycosylated glycerides having an HLB (hydrophilic-lipophilic balance) below 16; and
  a surfactant.

It also relates to a process for incorporating such a composition into the drinking water of livestock, characterized in that it comprises the following steps of:
  diluting said self-emulsifiable composition in the water of a dilution tank so as to form an emulsion; and
  incorporating said emulsion, at the desired dose, in the drinking water of livestock.

Finally, it relates to the use of a composition as defined above:
  as a drug for veterinary use;
  in the preparation of an emulsion capable of being diluted in drinking water in order to treat livestock; or
  to prepare a drug that can be administered orally, capable of being diluted in drinking water in order to prevent or treat diseases in livestock.

The self-emulsifiable composition according to the invention therefore has the special feature of forming, once incorporated in the water of the general distribution network during the intermediate dilution, an emulsion enabling good stability and homogeneity of the intermediate dilution to be ensured, and enabling total solubility of the active principle in the drinking water in the troughs and in the pipettes, where the animals come to drink, to be obtained quickly.

Figure 2:
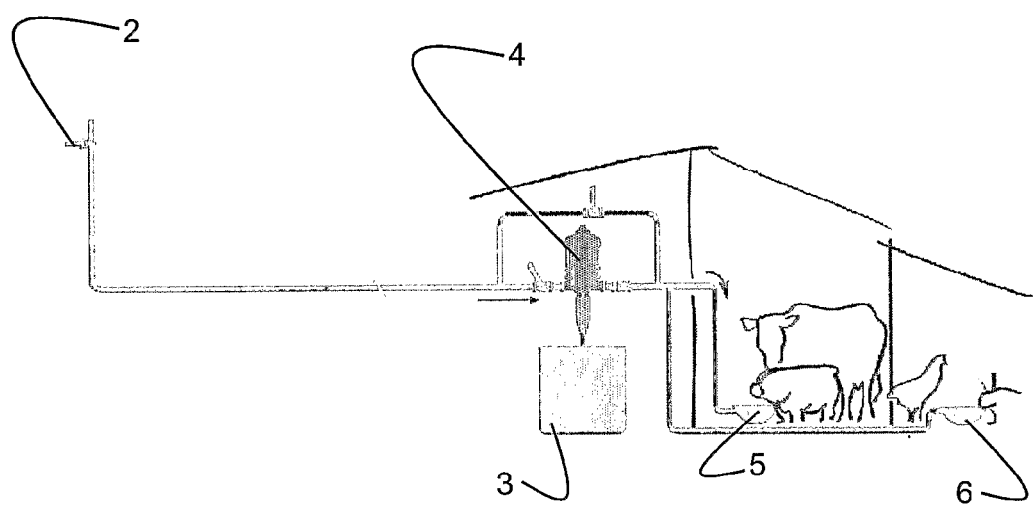
Figure 3:
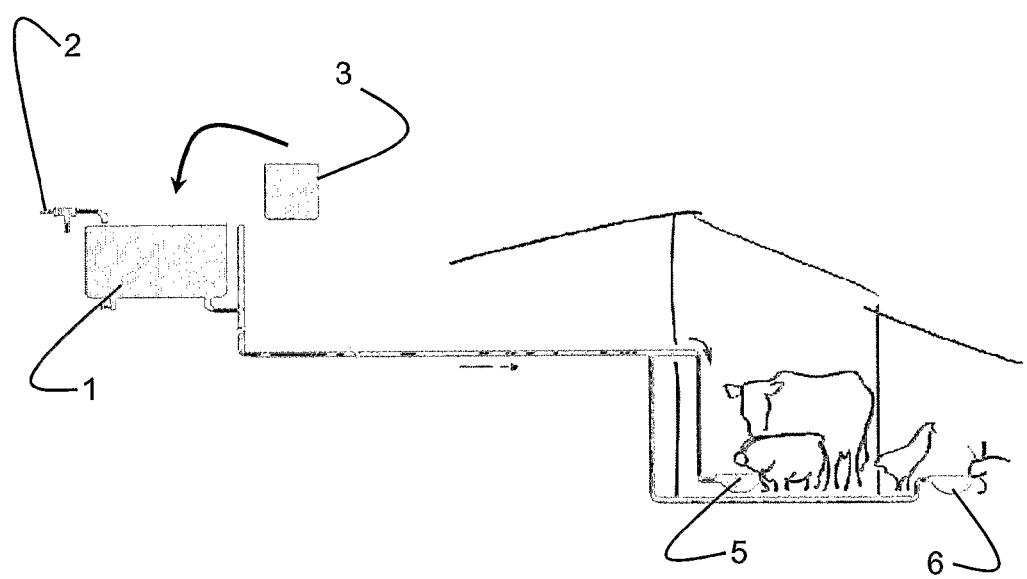

The invention can be better understood on reading the following non-limiting description and the appended drawings, in which FIGS. 1, 2 and 3 show different alternatives of drinking water circulation circuits for livestock.

The composition according to the invention is intended to be incorporated in the drinking water of livestock. This drinking water generally comes from a general water distribution network. It then passes through a circulation circuit. This circuit leads into troughs or pipettes. The livestock drink from these troughs or pipettes.

In the embodiment shown in FIG. 1, the circulation circuit is connected to the water distribution network 2. It comprises, immediately downstream of said network, a gravity tank 1. This tank 1 is capable of containing a large volume of water, sufficient to meet the drinking water requirements of animals for a determined period, preferably one day. It is connected, by a conduit, to a treatment dilution tank 3. This tank 3 is equipped with a dosing pump 4. The water extracted from the distribution network 2 flows into the gravity tank 1. To treat animals, the water contained in this tank 1 is brought to the pump 4. The pump is actuated. A calculated amount of treatment dilute contained in the tank 3 is then incorporated in the water circulating in the circuit. The circuit water, incorporating the dilute at the usage dose of the active principle contained in the composition according to the invention is finally emptied into the troughs 5 and/or pipettes 6 from which the animals drink. In general, the circulation of water in the circuit is automatically activated by control elements associated in particular with level sensors placed in the troughs 5 or pipettes 6, or with animal presence detectors.

In the embodiment shown in FIG. 2, the circulation circuit is similarly connected to the water distribution network 2. It does not however comprise a gravity tank, but only a treatment dilution tank 3 equipped with a dosing pump 4 actuated on demand for the treatment of animals.

Finally, in the embodiment shown in FIG. 3, the livestock drinking water circulation circuit does not have a dosing pump. The dilution tank 3 is separate from the circuit. The dilution of the composition according to the invention is performed in this separate tank, which is directly emptied into the gravity tank, at the usage dose of the active principle contained in the composition.

The self-emulsifiable composition according to the invention includes at least Florfenicol, a mixture of C8-C10 saturated polyglycosylated glycerides having an HLB (hydrophilic-lipophilic balance) below 16, and a surfactant. The invention therefore consists in particular of having selected a mixture of C8-C10 saturated polyglycosylated glycerides having an HLB (hydrophilic-lipophilic balance) below 16, which, in combination with specific surfactants, forms an emulsion in the presence of water supplied by the general distribution network.

According to the invention, by a mixture of C8-C10 saturated polyglycosylated glycerides having an HLB (hydrophilic-lipophilic balance) below 16, we mean a mixture of mono, di and triglycerides and mono and diesters of polyethylene glycol and C8-C10 fatty acid.

As a non-limiting example, the mixture of saturated polyglycosylated glycerides having an HLB (hydrophilic-lipophilic balance) below 16, we can cite the product sold by the Gattefosse company under the name "LABRASOL™".

LABRASOL™, also known as PEG-8 caprylic/capric glycerides, is a polyethoxylated derivative while also being a polyglycosylated derivative, a more general term. It should be noted that the term "polyglyco" in the word polyglycosylated refers to the oxycarbon chain in products such as esters or ethers of fatty acids, fatty alcohols and so on.

According to the invention, by surfactant, we mean a chemical composition having two groups, the first being polar or ionic, which has a high affinity for water, and the second containing a more or less long aliphatic chain, and which is hydrophobic. These chemical compounds are intended to cause the formation of micelles.

The surfactant is preferably chosen from the lipophilic esters of polyglycerol and the esters of propylene glycol engaging C8-C10 fatty acids. It is preferable to use oleic esters of polyglycerol, of the type sold by the Gattefosse company under the name "PLUROL OLEIQUE™", lauric esters of propylene glycol, such as that sold by the Gattefosse company under the trade name "LAUROGLYCOL™", and caprylic esters of propylene glycol, such as that sold by the Gattefosse company under the trade name "CAPRYOL 90™".

According to the invention, the ratio between the mixture of C8-C10 saturated polyglycosylated glycerides having an HLB (hydrophilic-lipophilic balance) below 16 and the surfactant is between 3 and 7 and preferably close to 5.

According to an advantageous embodiment of the invention, the composition includes:
- between 1 and 12% of the active principle Florfenicol by weight with respect to the total volume of the composition (w/v), preferably between 1.5 and 6% (weight/volume) of Florfenicol and even more preferably between 2 and 4% w/v of Florfenicol;
- at least 50% by weight with respect to the total volume of the composition (w/v) of the mixture of C8-C10 saturated polyglycosylated glycerides having an HLB (hydrophilic-lipophilic balance) below 16; and
- at least 5% by weight with respect to the total volume of the composition (w/v) of a surfactant.

According to a preferred embodiment of the invention, the surfactant has 5 to 40% by weight with respect to the total volume of the composition (w/v).

The mixture of C8-C10 saturated polyglycosylated glycerides having an HLB (hydrophilic-lipophilic balance) below 16 mentioned above is used to adjust, to the final volume required, the self-emulsifiable liquid composition. The weight/volume percentage of the C8-C10 saturated polyglycosylated glycerides having an HLB (hydrophilic-lipophilic balance) below 16 is dependent on the nature (therefore the density) thereof.

The composition according to the invention can also contain one or more additional non-ionic surfactants, miscible with water and physiologically acceptable, chosen from:
- hydrogenated ricin oil and ethylene oxide polyethers, or more specifically PEG-40 hydrogenated ricin oil or PEG-60 hydrogenated ricin oil, products known respectively by the trade names Cremophor RH40™ and Cremophor RH60™. Cremophor RH60™ is preferably used;
- polyoxyethylene-sorbitan monoesters, also known by the generic name polysorbates, monoesters with fatty acids such as lauric, palmitic, stearic and oleic acids. PEG-20 sorbitan monolaurate, PEG-20 sorbitan monopalmitate, PEG-20 sorbitan monostearate, PEG-20 sorbitan monooleate, products known respectively by the trade names Tween 20™, Tween40™, Tween60™ and Tween 80™ will preferably be used; Tween 80™ will preferably be used;
- fatty acid and oligo ethylene glycol esters, in particular with PEG-20 stearate and PEG-50 stearate, products known respectively by the trade names Simulsol M49™ and Simulsol M53™; and
- fatty acid and oligo ethylene glycol esters, in particular with PEG-20 hexadecanol, PEG dodecanol, PEG-20 octadecanol and PEG-20 oleyl alcohol, products known respectively by the trade names Simulsol M58™, Simulsol P4™, Simulsol 78™ and Simulsol 98™.

The composition according to the invention can also include solvents such as, in particular, glycol ethers, more specifically the ethylic ether of diethylene glycol, polyethylene-glycols, derivatives pyrrolidine-2-one, N-substituted (C1-C4) or not; preferably ethylic ether or diethylene glycol (Transcutol™), pyrrolidine-2-one (Soluphor P™) and N-methyl-2-pyrrolidone.

Finally, the composition according to the invention can also include auxiliary formulations such as antioxidants, preservatives, sweeteners or other appetizing agents regularly used and accepted for this type of composition.

Of course, a person skilled in the art will make sure to choose any component(s) to be added to these compositions and the respective amounts thereof so that the advantageous properties intrinsically associated with this invention are not substantially altered by the envisaged addition. For example, when a Florfenicol concentration of around 2.3% (weight/volume) is used, it is preferable to add a non-ionic surfactant to the composition as mentioned above, and when a concentration above 4.5% (weight/volume), or 6 to 10% (weight/volume) of Florfenicol for 100 ml is used, it is preferable to add a solvent as mentioned above.

According to a first preferred embodiment of the invention, the self-emulsifiable liquid composition is a stable solution including:
- 4 to 5 g of Florfenicol for 100 ml;
- 14 to 18 g of Lauroglycol™ for 100 ml; and
- 82 to 90 g of Labrasol™ for 100 ml.

According to a second preferred embodiment of the invention, the self-emulsifiable liquid composition is a stable solution including:
- 4 to 5 g of Florfenicol for 100 ml;
- 14 to 18 g of Plurol Oleique for 100 ml; and
- 82 to 90 g of Labrasol™ for 100 ml.

According to a third preferred embodiment of the invention, the self-emulsifiable liquid composition is a stable solution including:
- 2 to 3 g of Florfenicol for 100 ml;
- 11 to 13 g of Lauroglycol™ for 100 ml;
- 21 to 32 g of Plurol Oleique 80 for 100 ml; and
- 55 to 75 g of Labrasol™ for 100 ml.

The compositions according to the invention are used as a drug for veterinary use.

Thus, the invention also relates to the use of the composition according to the invention to prepare an emulsion capable of being diluted in drinking water in order to treat livestock. It also relates to the use of the composition according to the invention to prepare a drug capable of being diluted in drinking water in order to treat livestock according to the usual indications of Florfenicol, namely, for example, the preventive and curative treatment of respiratory tract infections due to *Mannheimia haemolytica*, *Pasteurella multocida* and *Histophilus somni* in cattle and the treatment of respiratory infections due to *Actinbacillus pleuropneumoniae* and *Pasteurella multocida* in pigs.

The following examples show this invention, more specifically with concrete examples of compositions according to the invention.

EXAMPLE 1

Compositions According to the Invention

| Composition 1 | |
|---|---|
| Name | Quantity |
| Florfenicol | 2.3 g |
| Lauroglycol | 12.6 g |
| Polysorbate 80 | 28.0 g |
| Labrasol | qsf 100 ml |

Composition 2

| Name | Quantity |
| --- | --- |
| Florfenicol | 2.3 g |
| Plurol Oleique | 12.4 g |
| Polysorbate 80 | 30.0 g |
| Labrasol | qsf 100 ml |

Composition 3

| Name | Quantity |
| --- | --- |
| Florfenicol | 4.5 g |
| Lauroglycol | 17.0 g |
| Labrasol | qsf 100 ml |

Composition 4

| Name | Quantity |
| --- | --- |
| Florfenicol | 4.5 g |
| Plurol Oleique | 17.2 g |
| Labrasol | qsf 100 ml |

Composition 5

| Name | Quantity |
| --- | --- |
| Florfenicol | 6.0 g |
| Lauroglycol | 12.4 g |
| Ethyl diglycol | 25.0 g |
| Labrasol | qsf 100 ml |

Composition 6

| Name | Quantity |
| --- | --- |
| Florfenicol | 8.0 g |
| Lauroglycol | 14.6 g |
| N-methyl-2-pyrrolidone | 20.0 g |
| Labrasol | qsf 100 ml |

Composition 7

| Name | Quantity |
| --- | --- |
| Florfenicol | 10.00 g |
| Lauroglycol | 11.95 g |
| Pyrrolidine-2-one | 30.00 g |
| Labrasol | qsf 100 ml |

EXAMPLE 2

Composition 1 described in example 1 was tested in detail for dilutions of 1 to 10 g/l, with dosages of active principle over 24 hours.

Stability of Florfenicol over time is observed for dilutions of 1 to 10 g/l, at room temperature, over a time period greater than 24 hours. In addition, no concentration gradient is observed in intermediate dilutions at rest when they are clear.

A concentration gradient is observed when the opacity noted for dilutions of between 1.0 and 3.3 g/l is accompanied by possible phase differences, at the theoretical concentration of 0.2 g/l. This gradient does not have immediate consequences: the coverage is 98.9% to 102.4% after 1 hour 30 minutes, then tends toward a balance, with particularly close results at 15 hours 30 minutes and 24 hours; coverage of 94.4% and 94.6% at the top; 93.4% and 94.9% at the middle; and 116.5% for both times at the bottom.

It can thus be considered that slight agitation, such as for example the flow caused by the suction pump, may ensure the homogeneity of the system.

Homogeneity of the dilution at 2 g/l is observed at room temperature after 15 hours when slight agitation is performed before the sample, regardless of the type of sample, with or without filtration (0.22 or 1 micron). This result confirms that the active principle appears in a colloidal form.

Compositions 5, 6 and 7 of example 1 were also evaluated in an aqueous dilution at concentrations of 2, 5 and 10 g/l. These compositions show physical stability over 8 days and more at 4° C. For the intermediate dilution at 2 g/l, a relatively slight opaque aspect, stable for 24 hours, is observed. For the intermediate dilution at 5 g/l, an opaque aspect denser than at 2 g/l is observed. For the intermediate dilution at 10 g/l, no changes are observed with respect to the intermediate dilution at 5 g/l.

EXAMPLE 3

We will now describe in detail the particularly attractive features of the self-emulsifiable compositions according to the invention containing 2.3% (weight/volume) Florfenicol.

a. Study of a Self-Emulsifiable Composition According to the Invention Containing 2.3% (Weight/Volume) Florfenicol Over 24 Hours.

Composition According to the Invention:

| | |
| --- | --- |
| Florfenicol | 23 mg |
| Excipients | qsf 1 ml |

Product Characteristics:
Preservation
   24 months
Dosage and Mode of Use in the Following Conditions:
   Temperature of around 25° C.
   Water hardness below 275 ppm
   In the Water Tank:
   To treat pigs from 8 to 200 kg, the Florfenicol concentration must be between 0.10 and 0.17 g/l of drink.

No obstacle is encountered for the envisaged concentrations. Indeed, the self-emulsifiable composition appears to be dilutable with a slight milkiness of the medium. In addition, the concentrations are below the solubility of Florfenicol, namely 1.32 g/l.

Dosing Pumps:

Four types of dosing pump equipment are envisaged: 1%, 2%, 5% and 10%.

A. 1% Dosing Pump:

To treat pigs from 8 to 200 kg, the Florfenicol concentration in the tank of the dosing pump must be between 10 and 16.7 g/l of water.

No problem is observed for the desired concentrations. Indeed the self-emulsifiable composition is dilutable. Moreover, certain concentrations appear beyond the "miscibility" of Florfenicol, namely 12 g/l.

B. 2% Dosing Pump:

To treat pigs from 8 to 200 kg, the Florfenicol concentration in the tank of the dosing pump must be between 5 and 8.3 g/l of water. No problem is observed for the desired concentrations. The self-emulsifiable composition appears to be dilutable.

C. 5% Dosing Pump:

To treat pigs from 8 to 200 kg, the Florfenicol concentration in the tank of the dosing pump must be between 2 and 3.3 g/l of water.

It is observed that at a concentration of 2 g/l, the medium is opaque but remains homogeneous. A phase difference appears after 6 hours. For concentrations above 2 g/l, the self-emulsifiable composition appears to be dilutable.

D. 10% Dosing Pump:

To treat pigs from 8 to 200 kg, the Florfenicol concentration in the tank of the dosing pump must be between 1 and 1.65 g/l of water.

Surprisingly, no problem is observed for the desired concentrations. The self-emulsifiable composition appears to be dilutable, giving an opaque homogeneous medium. Moreover, certain concentrations are below the solubility of Florfenicol, namely 1.32 g/l. At a concentration of 1.65 g/l, the medium is opaque and homogeneous, then a phase difference appears after 6 hours.

Conclusion:

It is indicated in the mode of use of the "Nuflor 2.3%" product sold by the Schering-Plough company that the solutions in which the Florfenicol concentrations are between 1.2 g/l and 12 g/l of Florfenicol settle. In consideration of the information presented above, it appears that, on the contrary, the self-emulsifiable composition according to the invention enables a homogeneous preparation to be obtained at these Florfenicol concentrations.

Additional tests have also made it possible to demonstrate that the composition according to the invention could be used in critical physical conditions. Thus, tests at a temperature of 5° C. and in the presence of hard water were performed and are conclusive.

b. Study of a Self-Emulsifiable Composition According to the Invention Containing 2.3% (Weight/Volume) Florfenicol Over 8 and 10 Hours in Critical Physical Conditions.

Composition According to the Invention:

| Florfenicol | 23 mg |
|---|---|
| Excipients | qsf 1 ml |

Product Characteristics:

Preservation 24 months

Dosage and Mode of Use Under the Following Conditions:

Temperature of around 5° C.

Water hardness between 370 and 375 ppm

In the Water Tank:

To treat pigs from 8 to 200 kg, the Florfenicol concentration must be between 0.10 and 0.17 g/l of drink.

No obstacle is encountered for the envisaged concentrations. Indeed, the self-emulsifiable composition appears to be dilutable with a slight milkiness of the medium. In addition, the concentrations are below the solubility of Florfenicol, namely 1.32 g/l.

Dosing Pumps:

Four types of dosing pump equipment are envisaged: 1%, 2%, 5% and 10%.

A. 1% Dosing Pump:

To treat pigs from 8 to 200 kg, the Florfenicol concentration in the tank of the dosing pump must be between 10 and 16.7 g/l of water.

The self-emulsifiable composition is dilutable.

B. 2% Dosing Pump:

To treat pigs from 8 to 200 kg, the Florfenicol concentration in the tank of the dosing pump must be between 5 and 8.3 g/l of water.

No problem is observed for the desired concentrations. The self-emulsifiable composition appears to be dilutable.

C. 5% Dosing Pump:

To treat pigs from 8 to 200 kg, the Florfenicol concentration in the tank of the dosing pump must be between 2 and 3.3 g/l of water.

It is observed that at the desired concentrations, the self-emulsifiable composition is dilutable, giving an opaque homogenous medium. Phase differences then appear after 6 hours.

D. 10% Dosing Pump:

To treat pigs from 8 to 200 kg, the Florfenicol concentration in the tank of the dosing pump must be between 1 and 1.65 g/l of water.

It is observed that at the desired concentrations, the self-emulsifiable composition is dilutable, giving an opaque homogenous medium.

CONCLUSION

These additional tests made it possible to demonstrate that the composition according to the invention could be used in critical physical conditions, i.e. in particular at a temperature of 5° C. and in the presence of water with a hardness of between 370 and 375 ppm.

In addition, when using pumps, for concentrations between 1.32 g/l and 12 g/l, it appears to be advantageous to maintain gentle agitation so as to enable the emulsion to remain perfectly homogeneous.

The invention claimed is:

1. A self-emulsifiable anhydrous liquid comprising:

2 to 4% of the active principle Florfenicol by weight with respect to the total volume of the composition;

82 to 90% of PEG-8 caprylic/capric glycerides ("LABRASOL™") by weight with respect to the total volume of the composition (w/v); and 14 to 18% of Polyglycerol oleate ("PLUROL OLEIQUE™") by weight with respect to the total volume of the composition (w/v), wherein said composition is stable and homogeneous at all dilution stages.

2. The composition according to claim 1, wherein the active principle Florfenicol represents 2.3% by weight with respect to the total volume of the composition.

* * * * *